United States Patent
Burkholz

(10) Patent No.: US 10,905,847 B2
(45) Date of Patent: Feb. 2, 2021

(54) INTEGRATED VASCULAR ACCESS DEVICE AND ANCHOR PAD

(71) Applicant: Becton, Dickinson and Company, Franklin Lakes, NJ (US)

(72) Inventor: Jonathan Karl Burkholz, Salt Lake City, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 15/481,716

(22) Filed: Apr. 7, 2017

(65) Prior Publication Data
US 2018/0289921 A1 Oct. 11, 2018

(51) Int. Cl.
*A61M 25/00* (2006.01)
*A61M 25/02* (2006.01)

(52) U.S. Cl.
CPC .......... *A61M 25/00* (2013.01); *A61M 25/02* (2013.01); *A61M 2025/0246* (2013.01); *A61M 2025/0253* (2013.01); *A61M 2025/0266* (2013.01); *A61M 2025/0273* (2013.01)

(58) Field of Classification Search
CPC .......... A61M 25/02; A61M 2025/0246; A61M 2025/0253; A61M 2025/0266; A61M 2025/0273; A61M 2025/026; A61M 2210/04; A61M 2210/12; A61M 2025/0213
USPC ........................................................ 604/180
See application file for complete search history.

(56) References Cited

U.S. PATENT DOCUMENTS

| | | | | |
|---|---|---|---|---|
| 3,670,727 A * | 6/1972 | Reiterman | ............ | A61M 5/158 604/177 |
| 3,856,020 A * | 12/1974 | Kovac | .................. | A61M 25/02 604/170.03 |
| 5,370,627 A | 12/1994 | Conway | | |
| 7,699,810 B2 * | 4/2010 | Rosenberg | ............ | A61M 25/02 604/180 |
| 8,747,360 B2 | 6/2014 | Peterson et al. | | |
| 9,155,867 B2 | 10/2015 | Peterson et al. | | |
| 9,199,062 B2 * | 12/2015 | Liska | ................ | A61M 25/0606 |
| 2004/0112510 A1 | 6/2004 | Rosenberg | | |
| 2013/0150796 A1 * | 6/2013 | Souza | ................ | A61F 13/0259 604/180 |
| 2016/0206855 A1 * | 7/2016 | Howell | .................. | A61M 25/02 |

FOREIGN PATENT DOCUMENTS

WO WO-2015035238 A1 * 3/2015 ............ A61M 5/158

* cited by examiner

*Primary Examiner* — Brandy S Lee
*Assistant Examiner* — Nidah M Hussain
(74) *Attorney, Agent, or Firm* — Kirton & McConkie; Craig Metcalf; Kevin Stinger

(57) ABSTRACT

An anchor system for securing a vascular access device to a patient may include an anchor pad, which may include a lower surface, an upper surface, and a window extending through the anchor pad. The system may also include the vascular access device, which may include a body and a stabilization platform extending from the body. The anchor pad may be coupled to and extend distally from the stabilization platform.

20 Claims, 5 Drawing Sheets

INTEGRATED VASCULAR ACCESS DEVICE AND ANCHOR PAD

BACKGROUND OF THE INVENTION

A clinician may insert a vascular access device into vasculature of a patient to infuse fluid and/or draw blood. The vascular access device may first penetrate skin of the patient at an insertion site, and when the vascular access device is properly placed within the vasculature, the clinician may apply a skin adhesive at the insertion site to secure the vascular access device. In order to apply the skin adhesive at the insertion site, the clinician may hold the inserted vascular access device in one hand and use another hand to open an adhesive container and apply the skin adhesive. After applying the skin adhesive to the insertion site, the clinician may hold the vascular access device while the skin adhesive dries. Securing the vascular access device via the skin adhesive may thus be a difficult and messy process that may result in dislodgement of the vascular access device, ineffective application of the skin adhesive through application of too much or too little of the skin adhesive, or adhering of the skin adhesive to a hand or glove of the clinician. Accordingly, there is a need in the art for devices, systems, and methods that provide securement of the vascular access device in a controlled, efficient and safe manner.

BRIEF SUMMARY OF THE INVENTION

The present disclosure relates generally to devices, systems, and associated methods to secure and stabilize a vascular access device inserted into a blood vessel of a patient. In some embodiments, an anchor system to secure the vascular access device to the patient may include an anchor pad, which may include a lower surface, an upper surface, and a window extending through the anchor pad. In some embodiments, the lower surface may include an adhesive layer to adhere the anchor pad to skin of the patient. In some embodiments, the window may provide access to the skin of the patient for application of a topical skin adhesive at an insertion site of the vascular access device, the insertion site being disposed within the window.

In some embodiments, the vascular access device may include a stabilization platform. In some embodiments, the stabilization platform may extend from a body of the vascular access device. For example, the vascular access device may include a peripheral intravenous (IV) catheter, which may include a catheter hub. In some embodiments, the stabilization platform may extend outwardly from the catheter hub. In some embodiments, the stabilization platform may include a first wing and/or a second wing. In some embodiments, the first and second wings may extend outwardly in opposite directions from the body of the vascular access device or the catheter hub.

In some embodiments, the anchor pad may extend distally from the stabilization platform. In some embodiments, the anchor pad and the stabilization platform may be integrated. In further detail, in some embodiments, the anchor pad may be coupled to the stabilization platform. In some embodiments, the anchor pad may be coupled to a bottom or top surface of the stabilization platform.

In some embodiments, the skin adhesive may be disposed within the window to secure the vascular access device in place at the insertion site. In some embodiments, the window may enclose the insertion site, which may facilitate controlled and contained application of the skin adhesive at the insertion site. In further detail, the skin adhesive may contact the anchor pad and/or the skin of the patient within the window. In some embodiments, the skin adhesive may be prevented or discouraged from contacting skin of the patient outside of the window, reducing a likelihood of a messy application of the skin adhesive. In some embodiments, the skin adhesive may provide localized stabilization of the vascular access device at the insertion site and/or may provide a seal around the vascular access device at the insertion site, which may prevent infection. The skin adhesive may also increase indwell time for the vascular access device.

In some embodiments, the anchor pad may include a release liner that may cover the adhesive layer and may be removed prior to adhering the anchor pad to the skin of the patient. In some embodiments, an entirety of the adhesive layer may be adhered to the skin of the patient at approximately the same time. In some embodiments, portions of the adhesive layer may be adhered to the skin of the patient at different times. For example, a portion of the adhesive layer configured to be disposed between the skin and the stabilization platform may be adhered to the skin prior to a fold portion of the anchor pad. In these and other embodiments, a portion of the release liner corresponding to the foldable portion may be removed at a same time as or after a portion of the release liner corresponding to the portion of the adhesive layer configured to be disposed between the skin and the stabilization platform.

In some embodiments, the anchor pad may be foldable. For example, prior to inserting the vascular access device into the patient at the insertion site, the anchor pad may be folded such that a fold portion of the anchor pad is disposed in a first or proximal position. The fold portion may correspond to a portion of the adhesive layer. After inserting the vascular access device into the patient at the insertion site, the anchor pad may be unfolded such that the fold portion is disposed in a second or distal position in which the portion of the adhesive layer contacts the skin of the patient.

In some embodiments, a method of securing the vascular access device may include providing the vascular access device, which may include the stabilization platform. In some embodiments, the method may include coupling the vascular access device to the anchor pad. In some embodiments, the method may include inserting the vascular access device into the patient at the insertion site. In some embodiments, the method may include adhering the anchor pad to the skin of the patient via the adhesive layer. In some embodiments, the method may include applying the skin adhesive at the insertion site and/or proximate the insertion site within the window after the vascular access device is inserted at the insertion site and after the anchor pad is adhered to the skin of the patient. In some embodiments, adhering the anchor pad to the skin of the patient via the adhesive layer may include removing the release liner covering the adhesive layer.

In some embodiments, the method may include, prior to inserting the vascular access device into the patient at the insertion site, folding the anchor pad such that the fold portion of the anchor pad is disposed in the first or proximal position. In these and other embodiments, the method may include removing a release liner covering a portion of the adhesive layer corresponding to the fold portion of the anchor pad. In some embodiments, the method may include, after inserting the catheter assembly into the patient at the insertion site, unfolding the anchor pad such that the fold portion is disposed in the second or distal position in which the portion of the adhesive layer contacts skin of the patient.

BRIEF DESCRIPTION OF THE SEVERAL VIEWS OF THE FIGURES

In order that the manner in which the above-recited and other features and advantages of the invention will be readily understood, a more particular description of the devices, systems, and associated methods to secure and stabilize a vascular access device briefly described above will be rendered by reference to specific embodiments thereof, which are illustrated in FIGS. 1-4. Understanding that these Figures depict only typical embodiments and are not, therefore, to be considered to be limiting of its scope, the invention will be described and explained with additional specificity and detail through the use of the accompanying Figures in which.

DETAILED DESCRIPTION OF THE INVENTION

It will be readily understood that the components of the present invention, as generally described and illustrated in the Figures in the present disclosure, could be arranged and designed in a wide variety of different configurations. Thus, the following more detailed description of the embodiments, represented in FIGS. 1-4, is not intended to limit the scope of the invention, as claimed, but is merely representative of some embodiments of the invention.

Figure 1:
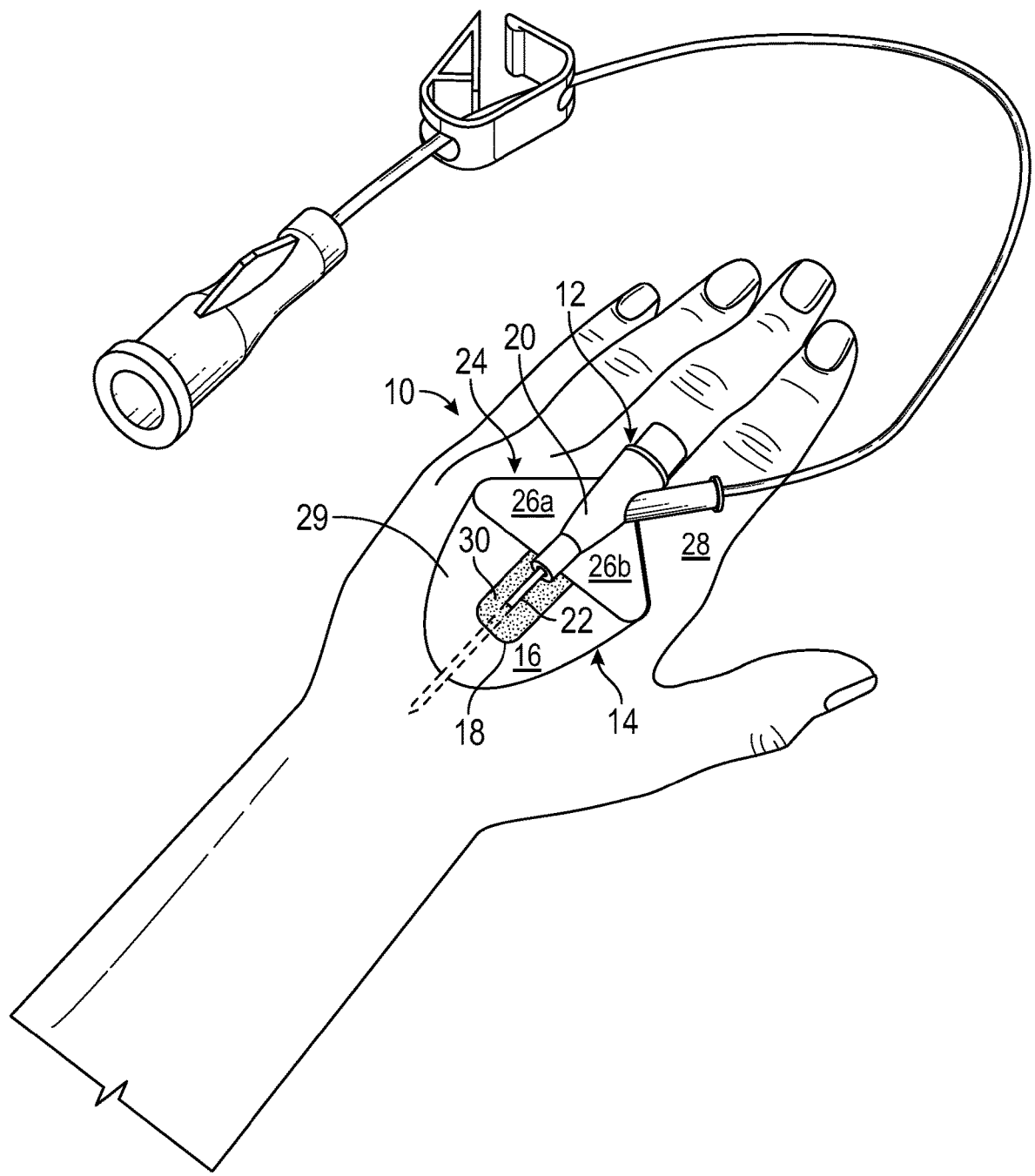
FIG. 1 is an upper perspective view of an example anchor system secured to a patient, according to some embodiments.

Referring to FIG. 1, an example anchor system 10 for securing a catheter assembly 12 to a patient is illustrated. It is understood, however, that the anchor system 10 may be utilized in connection with other vascular access devices, including, but not limited to, fluid supply and drainage lines, feeding tubes, chest tubes, scopes, connectors, adaptors, electrical wires and cables, and the like, any of which may be secured to the patient by the anchor system 10.

In some embodiments, the anchor system 10 may include an anchor pad 14, which may include various shapes and sizes. In some embodiments, the anchor pad 14 may include a lower surface, an upper surface 16, and a window 18 extending through the anchor pad 14.

In some embodiments, the anchor system 10 may include the catheter assembly 12. In some embodiments, the catheter assembly 12 may include a catheter hub 20 configured to house a catheter 22. An introducer needle is typically inserted through the catheter 22 such that a tip of the needle extends beyond a tip of the catheter 22. Insertion of the needle into a blood vessel of the patient provides an opening into the blood vessel through which the tip of the catheter 22 is inserted. Once the catheter 22 is inserted into the blood vessel of the patient, the introducer needle is removed from a lumen of the catheter 22 to permit infusion or withdrawal via the catheter 22. In some embodiments, the anchor system 10 may secure or stabilize the catheter 22 within the blood vessel of the patient, as illustrated in FIG. 1.

In some embodiments, the catheter assembly 12 may include a stabilization platform 24. In some embodiments, the stabilization platform 24 may extend outwardly from the catheter hub 20. In some embodiments, the stabilization platform 24 may include a first wing 26a and/or a second wing 26b. In some embodiments, the first wing 26a and/or second wing 26b may extend outwardly in opposite directions from the catheter hub 20.

In some embodiments, the stabilization platform 24 may be configured to rest on the skin 28 of the patient when the catheter 22 is inserted at the insertion site in a fluid delivery configuration, as illustrated in FIG. 1. In some embodiments, the stabilization platform 24 may support one or more digits of the clinician as the clinician inserts the catheter 22 at the insertion site and/or moves the catheter assembly 12 from an insertion configuration, illustrated in FIGS. 2A and 2B, to the fluid delivery configuration, illustrated in FIG. 1. In some embodiments, the clinician may pinch or grip the stabilization platform 24.

Figure 2A:
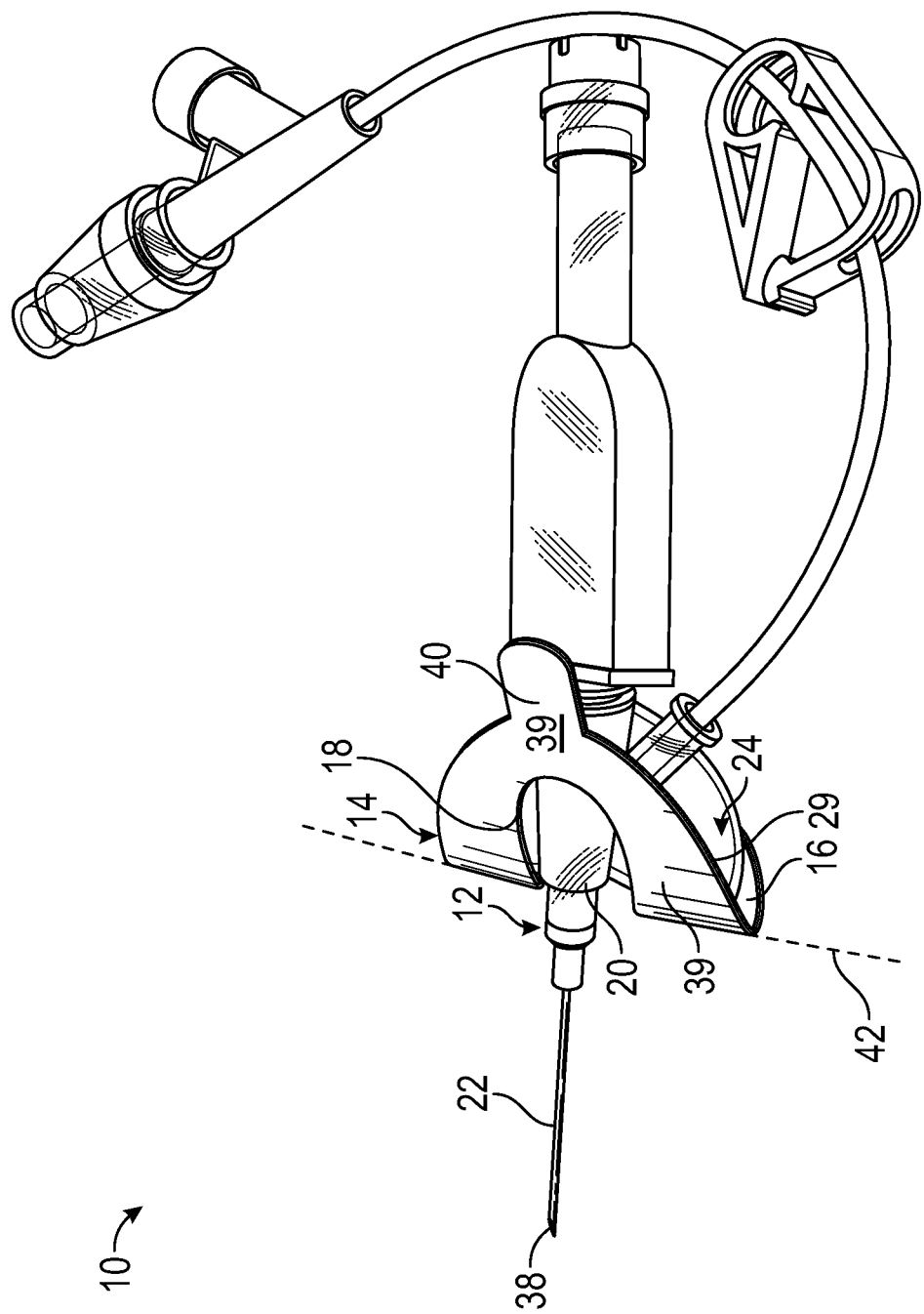
FIG. 2A is an upper perspective view of the anchor system of FIG. 1 prior to insertion into a blood vessel of the patient, according to some embodiments.
Figure 2B:
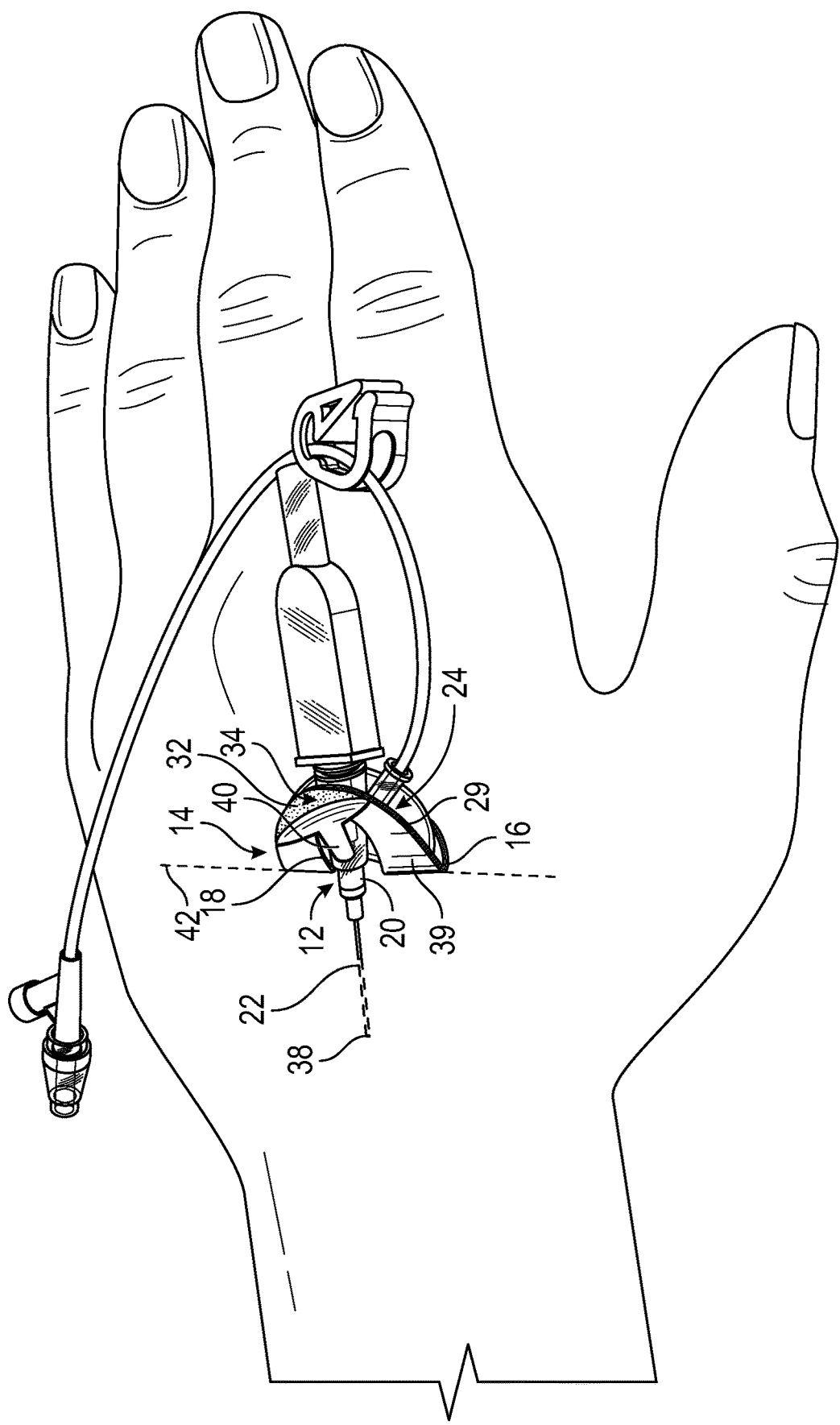
FIG. 2B is an upper perspective view of the anchor system of FIG. 1 inserted into the blood vessel of the patient, illustrating a release liner partially removed, according to some embodiments.

In some embodiments, the anchor pad 14 may extend distally from the stabilization platform 24. In some embodiments, the anchor pad 14 and the stabilization platform 24 may be integrated. In further detail, in some embodiments, the anchor pad 14 may be coupled to the stabilization platform 24. In some embodiments, the anchor pad 14 may be coupled to any surface of the stabilization platform 24. In a preferred embodiment, the anchor pad 14 may be coupled to a bottom surface of the stabilization platform 24, as illustrated in FIGS. 1-3. In some embodiments, the anchor pad 14 may be coupled to a top surface of the stabilization platform 24. In some embodiments, the anchor pad 14 may fully or partially cover the top or bottom surface of the stabilization platform 24. The anchor pad 14 may be coupled to the stabilization platform 24 in any number of ways, such as, for example, adhesive, ultrasonic welding, heat staking, insert molding, etc.

In some embodiments, the window 18 may provide access to skin 28 of the patient for application of a topical skin adhesive 30 at an insertion site of the catheter assembly 12, the insertion site being disposed within the window 18. In some embodiments, the skin adhesive 30 may be disposed within the window 18 to secure the catheter assembly 12 in place at the insertion site. In some embodiments, the window 18 may enclose the insertion site, which may facilitate controlled and contained application of the skin adhesive 30 at the insertion site. In further detail, the skin adhesive 30 may contact the skin 28 of the patient within the window 18 and/or a portion of the anchor pad 14 proximate the window 18, but may be prevented or discouraged from contacting the skin 28 of the patient outside of the window 18 and/or beyond an outer edge of the anchor pad, reducing a likelihood of a messy application of the skin adhesive 30. In some embodiments, the skin adhesive 30 may provide localized stabilization of the catheter assembly 12 at the insertion site and/or may provide a seal around the catheter assembly 12 at the insertion site, which may prevent infection. The skin adhesive 30 may also increase an indwell time for the catheter assembly 12. In some embodiments, the skin adhesive 30 and/or the integrated anchor pad 14 and catheter assembly 12 may increase a force necessary to dislodge the catheter assembly 12 at the insertion site.

In some embodiments, the catheter assembly 12 may be inserted into the patient prior to application of the skin adhesive 30 to the insertion site. Given the difficultly and usability challenges of holding the catheter assembly 12 in position while applying the skin adhesive 30 to the insertion site, it may be advantageous to provide a means of securement of the catheter assembly 12, such as the integrated anchor pad 14, prior to application of the skin adhesive 30.

Thus, in some embodiments, insertion of the catheter assembly 12 and placement of the anchor pad 14 on the skin of the patient in an unfolded position, as illustrated in FIG. 1, may occur prior to application of the skin adhesive 30. The anchor pad 14 coupled to the catheter assembly 12 and at least a fold portion 29 adhered to the skin 28 of the patient via an adhesive layer may facilitate greater control and accuracy in placement of the skin adhesive 30 at the insertion site, reduce an amount of skin adhesive 30 required, reduce a likelihood of a messy application of the skin adhesive 30, and reduce a risk of the catheter assembly 12 becoming dislodged due to unintentional movement during application of the skin adhesive 30. Further, the anchor pad 14 coupled to the catheter assembly 12 and adhered to the skin 28 of the patient may eliminate a need for the clinician to hold the catheter assembly 12 while the skin adhesive 30 dries, which may reduce a likelihood of the skin adhesive 30 bonding to a hand or glove of the clinician.

In some embodiments, an outer edge of the window 18 may be spaced apart from the outer edge of the anchor pad 14. In further detail, in some embodiments, the window 18 may be inset from the outer edge of the anchor pad 14. In some embodiments, the catheter assembly 12 may extend through a middle portion of the window 18.

In some embodiments, the skin adhesive 30 may include cyanoacrylate or another suitable glue or bonding material. In some embodiments, cyanoacrylate may include liquid monomers and may polymerize on contact with the skin, creating a flexible and/or semi-rigid layer. In these and other embodiments, liquid cyanoacrylate may be applied at the insertion site within the window 18 and may cure to a solid form within a period of seconds.

Referring now to FIGS. 2A-2D, in some embodiments, the lower surface 34 may include the adhesive layer 32 to adhere the anchor pad 14 to skin 28 of the patient. In some embodiments, the adhesive layer 32 may include any type or form of adhesive that is suitable for use with the methods and embodiments discussed in the present disclosure. In some embodiments, the adhesive layer 32 may be a spray-on adhesive, adhesive film, or any other type of adhesive application. In some embodiments the adhesive layer 32 may be formed of or include a polymer-based pressure sensitive adhesive. For example, when a polymer-based pressure sensitive adhesive is used in the adhesive layer 32, a bond may formed between the adhesive layer 32 and the skin 28 of the patient by applying light pressure between anchor pad 14 and the skin 28. In some embodiments, the adhesive layer 32 may include a slight liquid carrier that facilitates bonding with the skin 28. In some embodiments, the adhesive layer 32 may include a single-use glue, such that the adhesive layer 32 loses its adhesive properties once removed from the skin 28. In some embodiments, the adhesive layer 32 may include an antimicrobial agent to aid in maintaining sterility of the insertion site. In some embodiments, the adhesive layer 32 may include a multiple-use glue, which may allow the anchor pad 14 to be applied repeatedly.

In some embodiments, the anchor pad 14 may include a release liner 36 that may cover the adhesive layer 32 and may be removed prior to adhering the anchor pad 14 to the skin 28 of the patient. In some embodiments, the release liner 36 may include any material or combination of materials that permit temporary bonding between the release liner 36 and the adhesive layer 32.

In some embodiments, an entirety of the adhesive layer 32 may be adhered to the skin of the patient at approximately a same time. In some embodiments, portions of the adhesive layer 32 may be adhered to the skin 28 of the patient at different times. For example, a portion of the adhesive layer 32 configured to be disposed between the skin 28 and the stabilization platform 24 may be adhered to the skin 28 prior to the fold portion 29 of the anchor pad 14. In these and other embodiments, a portion of the release liner corresponding to the fold portion 29 may be removed at a same time as or after a portion of the release liner 36 corresponding to the portion of the adhesive layer 32 configured to be disposed between the skin 28 and the stabilization platform 24.

Figure 2C:
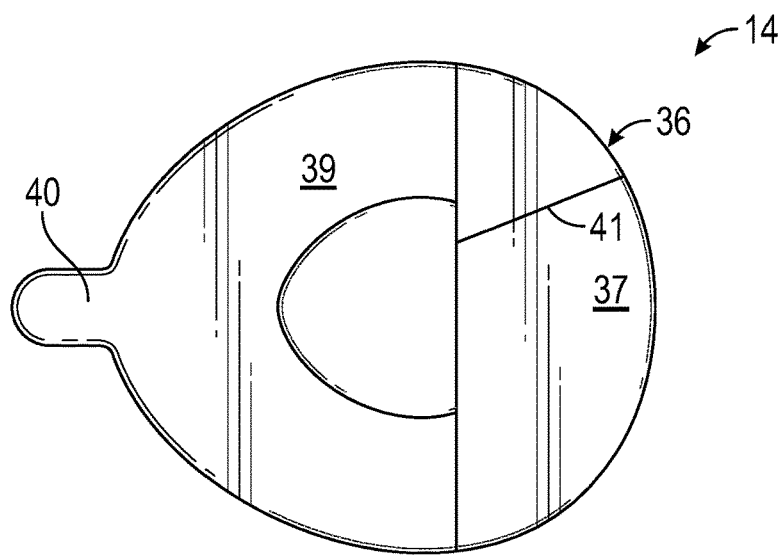
FIG. 2C is a bottom view of an example anchor pad of the anchor system of FIG. 1, according to some embodiments.
Figure 3:
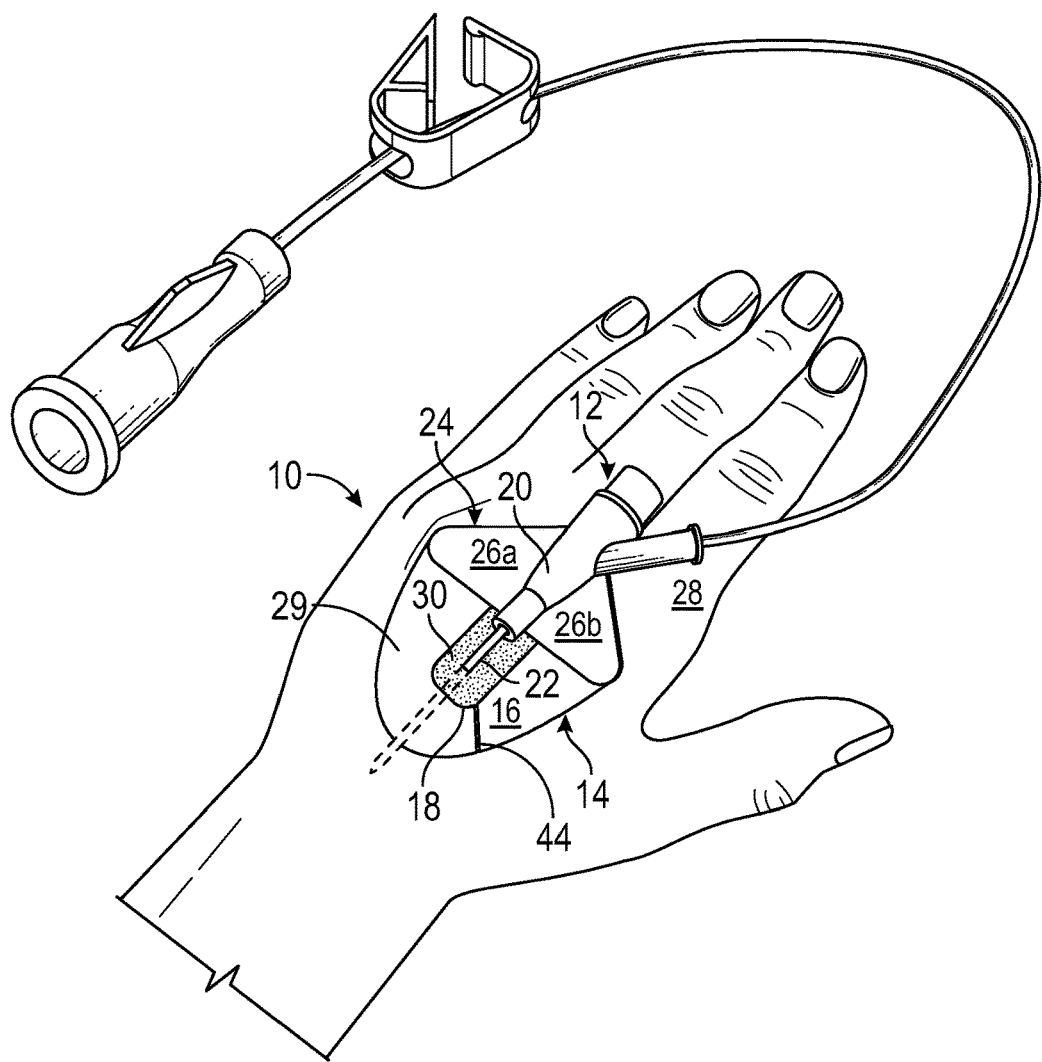
FIG. 3 is an upper perspective view of the anchor system of FIG. 1, illustrating an example slot, according to some embodiments.

As illustrated in FIG. 2C, in some embodiments, the release liner 36 may be divided into multiple pieces or sections to ease attachment of the anchor pad 14 to the skin 28 of the patient. In some embodiments, the release liner 36 may include a first section 37 corresponding to the portion of the adhesive layer 32 configured to be disposed between the skin 28 and the stabilization platform 24. In some embodiments, the release liner 36 may include a second section 39 corresponding to the fold portion 29. In some embodiments, the first and second sections 37, 39 may be removed separately. In some embodiments, the second section 39 may include a slit or slot 41, which may allow for the second section 39 to be removed in a distal direction after the catheter assembly 12 is inserted into the patient at the insertion site.

In some embodiments, the release liner 36 may include an aperture corresponding to the window 18 or the release liner 36 may cover the window 18. In some embodiments, the release liner 36 may include paper, plastic, or another suitable material. In some embodiments, the release liner 36 may include one or more antimicrobial agents.

In some embodiments, the release liner 36 may be removed from the adhesive layer 32 by pulling in a distal direction on the release liner 36, which may reduce a risk of dislodging the catheter 22. In some embodiments, the release liner 36 may include one or more pull-tabs 40 to facilitate removal of the release liner 36 from the adhesive layer 32. In some embodiments, the pull-tabs 40 may be designed in a variety of configurations and need not be disposed along a centerline of the anchor pad 14.

FIG. 2A illustrates the integrated anchor pad 14 and catheter assembly 12 prior to inserting the catheter assembly 12 into the patient at the insertion site. The tip of the introducer needle 38 extends beyond a tip of the catheter 22 prior to and during the insertion of the catheter assembly 12. As mentioned, in some embodiments, the anchor pad 14 may be foldable. In some embodiments, prior to inserting the catheter assembly 12 into the patient at the insertion site, the anchor pad 14 may be folded such that the fold portion 29 of the anchor pad 14 is disposed in a first or proximal position, illustrated in FIG. 2A. In some embodiments, after inserting the vascular access device into the patient at the insertion site, the anchor pad 14 may be unfolded such that the fold portion 29 is disposed in a second or distal position in which a portion of the adhesive layer 32 corresponding to the fold portion 29 contacts the skin 28, as illustrated in FIG. 1.

The adhesive layer 32 may cover all or a portion of the lower surface 34 of the anchor pad 14. In some embodiments, a particular portion of the lower surface 34 configured to be disposed between the bottom surface of the stabilization platform 24 and the skin 28 may not include the adhesive layer 32. In some embodiments, the particular portion of the lower surface 34 configured to be disposed between the bottom surface of the stabilization platform 24 and the skin 28 may include the adhesive layer 32, which may allow the particular portion to be secured to the skin 28 prior to unfolding the anchor pad 14. In some embodiments, the release liner 26 may be divided along a fold line 42, which may allow the first section 37 to be removed at a different time as or before a remaining portion of the adhesive layer 32.

In some embodiments, the window 18 may provide access to the skin 28 of the patient for application of the skin adhesive 30 and/or a cleaning or disinfection agent at the insertion site of the catheter assembly 12. In some embodiments, the cleaning agent may be disposed within the window 18 and may contact the skin 28 of the patient within the window 18. In some embodiments, the cleaning agent may be prevented or discouraged from contacting the skin 28 of the patient outside of the window 18 and/or beyond an outer edge of the anchor pad 14. In some embodiments, the skin adhesive and/or the cleaning agent may be wicked or pulled into the anchor pad 14 from the window 18 but may not contact the skin 28 beyond the outer edge of the anchor pad 14.

In some embodiments, a material of the anchor pad 14 may absorb a portion of the skin adhesive 30 and/or the cleaning agent and prevent spreading of the skin adhesive 30 and/or cleaning agent beyond the outer edge of the anchor pad 14. In some embodiments, the skin adhesive 30 and/or the cleaning agent may be contained within the window 18. In some embodiments, the anchor pad 14 may include any suitable medical grade material. In some embodiments, in addition to the adhesive layer 32, the anchor pad 14 may include a cloth layer and/or a foam layer. In some embodiments, the cloth layer may include the upper surface 16. In some embodiments, the foam layer may include the upper surface 16. In some embodiments, the cloth layer may be non-woven or woven. In some embodiments, the anchor pad 14 may include one or more antimicrobial agents, which may be applied in a film or otherwise.

Referring now to FIG. 3, in some embodiments, the anchor pad 14 may include a slit or slot 44 that may extend from the window 18 to an exterior of the anchor pad 14. In some embodiments, the slot 44 may facilitate or ease insertion of the catheter assembly 12 into the patient prior to unfolding the anchor pad 14 such that the fold portion 29 of the anchor pad 14 is moved from the first position to the second position to be adhered to the skin 28 of the patient.

FIGS. 1-3 illustrate a peripheral IV catheter similar to the BD NEXIVA™ Closed IV Catheter (Becton, Dickinson and Company). However, it is understood that the anchor system 10 may be utilized in connection with various types of catheter assemblies and vascular access devices. The anchor system 10 may be utilized in connection with, for example, peripheral IV catheters, central venous catheters (CVCs), peripherally inserted central catheters (PICCs), hemodialysis catheters, arterial catheters, integrated IV catheters, non-integrated IV catheters, etc. The anchor system 10 may also be utilized in connection with BD SAF-T-INTIMA™ Closed IV Catheter (Becton, Dickinson and Company).

Figure 4:
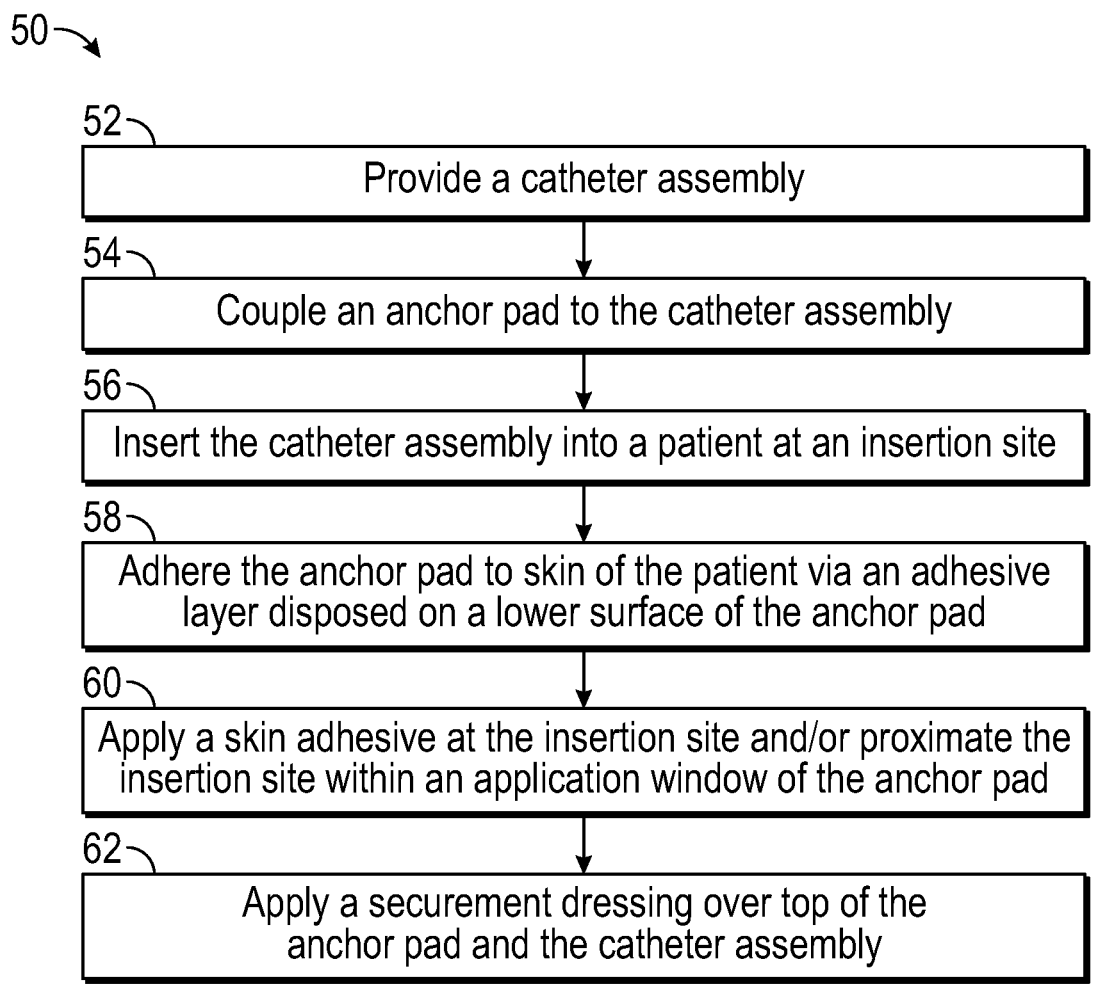
FIG. 4 is a block diagram of an example method of securing a catheter, according to some embodiments.

Referring now to FIG. 4, in some embodiments, a method 50 of securing a catheter may begin at block 52. At block 52, a catheter assembly may be provided. In some embodiments, the catheter assembly may include a stabilization platform. The catheter assembly, catheter, and stabilization platform may include or correspond to the catheter assembly 12, the catheter 22, and the stabilization platform 24, respectively, discussed with respect to any of FIGS. 1-3. Block 52 may be followed by block 54.

At block 54, an anchor pad may be coupled to the catheter assembly. The anchor pad may include or correspond to the anchor pad 14 discussed with respect to any of the previous FIGS. 1-3. Block 54 may be followed by block 56.

At block 56, the catheter assembly may be inserted into a patient at an insertion site. In some embodiments, once a distal tip of the catheter of the catheter assembly is properly placed into a blood vessel of the patient and an introducer needle is withdrawn from the blood vessel and the distal tip, the catheter may be left in place to provide intravenous access to the patient. Block 56 may be followed by block 58.

At block 58, the anchor pad may be adhered or attached to the skin of the patient via an adhesive layer disposed on a lower surface of the anchor pad. In some embodiments, adhering the anchor pad via the adhesive layer may include unfolding the anchor pad and/or securing a portion of the anchor pad surrounding a window to the skin of the patient. The adhesive layer may correspond to the adhesive layer 32 discussed with respect to any of the previous FIGS. 1-3. Block 58 may be followed by block 60.

At block 60, a skin adhesive may be applied at the insertion site and/or proximate the insertion site within the window. In some embodiments, the skin adhesive may be wicked or pulled into the anchor pad from the window. In these and other embodiments, the skin adhesive may not contact the skin beyond an outer edge or perimeter of the anchor pad. In some embodiments, a material of the anchor pad may absorb the skin adhesive to prevent spreading of the skin adhesive beyond the outer edge of the anchor pad. For example, the anchor pad may include one or more of the following: a cloth layer, a foam layer, and another absorbing layer. In some embodiments, the cloth layer may be non-woven or woven. In some embodiments, the anchor pad may help limit spread of the skin adhesive beyond the outer edge of the anchor pad but may not completely prevent the skin adhesive from contacting the skin of the patient beyond the outer edge of the anchor pad. In some embodiments, the skin adhesive may be applied after the catheter is inserted at the insertion site and the anchor pad is adhered to the skin of the patient. The skin adhesive may correspond to the skin adhesive 30 discussed with respect to any of the previous FIGS. 1-3. Block 60 may be followed by block 62.

At block 62, a securement dressing may be applied over top of the anchor pad and the catheter assembly. In some embodiments, the securement dressing may include an antimicrobial agent, such as, for example, TEGADERM™ or CHLORASHIELD™.

Although illustrated as discrete blocks, various blocks may be divided into additional blocks, combined into fewer blocks, or eliminated, depending on the desired implementation. Furthermore, the order of the blocks may be changed. Also, additional blocks may be added. In some embodiments, the method may include, prior to inserting the vascular access device into the patient at the insertion site, folding the anchor pad such that a fold portion of the anchor pad is disposed in a first position. In these and other embodiments, the method may include removing a release liner covering a portion of the adhesive layer corresponding to the fold portion of the anchor pad. In some embodiments, the method may include, after inserting the catheter assembly into the patient at the insertion site, unfolding the anchor pad such that the fold portion is disposed in a second position in which the portion of the adhesive layer contacts skin of the patient.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method of securing a catheter assembly, the method comprising:
providing the catheter assembly comprising a catheter hub, a stabilization platform extending from the catheter hub, a catheter that extends distally from the catheter hub, and an anchor pad having an upper surface and a bottom surface opposite the upper surface, the bottom surface forming an adhesive surface, the anchor pad including a connected portion that is coupled to the stabilization platform and a fold portion that extends distally from the connected portion, the fold portion being folded back overtop the stabilization platform such that a portion of the bottom surface is oriented upwardly, the fold portion of the anchor pad including a window, wherein the fold portion is folded along a fold line, wherein the fold line extends through the window;
while the fold portion is folded back in a proximal direction overtop the stabilization platform, inserting a distal tip of the catheter into a vasculature of a patient;
unfolding the fold portion onto skin surrounding an insertion site of the catheter to thereby cause the insertion site of the catheter to be positioned within the window; and
applying a skin adhesive to the insertion site via the window.

2. The method of claim 1, wherein an outer edge of the window is spaced apart from an outer edge of the anchor pad.

3. The method of claim 1, wherein an upper surface of the connected portion is coupled to a bottom surface of the stabilization platform.

4. The method of claim 1, wherein the connected portion is coupled to a top surface of the stabilization platform.

5. The method of claim 1, wherein the fold line is positioned distal to a distal end of the stabilization platform.

6. The method of claim 1, wherein the anchor pad further comprises a release liner adhered to the adhesive surface.

7. The method of claim 6, wherein the release liner includes a first section that is adhered to a first portion of the adhesive surface and a second section that is adhered to a second portion of the adhesive surface, wherein the connected portion includes the first portion of the adhesive surface, wherein the fold portion includes the second portion of the adhesive surface.

8. The method of claim 7, wherein the second section extends to the fold line along which the fold portion is folded.

9. The method of claim 7, wherein the second section includes one or more pull tabs.

10. The method of claim 7, wherein the second section includes a slit or a slot.

11. The method of claim 1, wherein the anchor pad is formed of a cloth or a foam material that is configured to absorb the skin adhesive.

12. The method of claim 1, wherein the window extends proximally to the stabilization platform.

13. The method of claim 1, wherein the connected portion of the anchor pad is coupled to a top surface or a bottom surface of the stabilization platform.

14. The method of claim 1, wherein the window is inset from an outer edge of the anchor pad.

15. The method of claim 1, wherein the stabilization platform includes a first wing and a second wing that are coupled to the anchor pad such that the first wing and the second wing are directly adjacent to the window.

16. The method of claim 15, wherein a bottom surface of the first wing and a bottom surface of the second wing are coupled to the anchor pad.

17. The method of claim 1, further comprising releasing the catheter assembly prior to the skin adhesive drying.

18. The method of claim 1, wherein the anchor pad further comprises a slot that extends from the window to an exterior of the anchor pad.

19. A method of securing a catheter assembly comprising:
providing a catheter assembly that comprises a catheter hub, a stabilization platform extending from the catheter hub, and a catheter that extends distally from the catheter hub;
providing an anchor pad having an upper surface and a bottom surface opposite the upper surface, the bottom surface forming an adhesive surface, the anchor pad including a connected portion that is coupled to the stabilization platform and a fold portion that extends distally from the connected portion, the fold portion including a window and a fold line that extends through the window;
folding the fold portion along the fold line back overtop the stabilization platform prior to insertion of the catheter such that a portion of the bottom surface is oriented upwardly;
inserting the catheter;
after insertion of the catheter, unfolding the fold portion onto skin surrounding an insertion site of the catheter to cause the insertion site to be positioned within the window.

20. The method of claim 19, wherein the fold line is positioned distal to a distal end of the stabilization platform.

* * * * *